United States Patent
Masui et al.

(10) Patent No.: US 8,435,955 B2
(45) Date of Patent: May 7, 2013

(54) ANTIBACTERIAL DEODORANT

(76) Inventors: Yoshiharu Masui, Nagoya (JP); Atsuko Tomida, Yokkaichi (JP); Hideo Hirata, Nagoya (JP); Koichi Otsuki, Kyoto (JP)

(*) Notice: Subject to any disclaimer, the term of this patent is extended or adjusted under 35 U.S.C. 154(b) by 530 days.

(21) Appl. No.: 12/584,577

(22) Filed: Sep. 8, 2009

(65) Prior Publication Data

US 2010/0160242 A1    Jun. 24, 2010

(30) Foreign Application Priority Data

Sep. 12, 2008   (JP) ................. 2008-234776

(51) Int. Cl.
   *C07K 5/062*   (2006.01)
(52) U.S. Cl.
   USPC ...................... 514/21.91; 562/575
(58) Field of Classification Search ............ 514/21.91; 562/575
   See application file for complete search history.

(56) References Cited

U.S. PATENT DOCUMENTS

| | | | | |
|---|---|---|---|---|
| 4,078,055 | A | * | 3/1978 | Naganuma et al. .......... 424/76.6 |
| 4,337,269 | A | * | 6/1982 | Berke et al. .................... 514/494 |
| 5,234,909 | A | * | 8/1993 | Philippe ........................ 514/18.8 |
| 5,942,635 | A | * | 8/1999 | Ehle et al. ........................ 554/69 |

OTHER PUBLICATIONS

Abstract of Miyake, JP 3529059, Jul. 1996.*

* cited by examiner

*Primary Examiner* — David Lukton
(74) *Attorney, Agent, or Firm* — Flynn, Thiel, Boutell & Tanis, P.C.

(57) ABSTRACT

By selecting one or more deodorizing agents from among glycine, cysteine and glycylglycine, and incorporating the selected deodorizing agent(s) and a surfactant, the toxicity of the surfactant to men and beasts is controlled without inhibiting the antibacterial actions that the surfactant has inherently. Glycine, cysteine, and glycylglycine each have a strong deodorizing action. The invention causes antibacterial deodorants to further have a deodorizing action by using such deodorizing agents. Moreover, the invention increases the permeating ability, thereby enhancing both the antibacterial action and the deodorizing action by subjecting water to treatment for fragmenting a cluster of the water and then adding the resulting active water as a diluent, or by preparing the diluent by incorporating alcohol with the active water.

6 Claims, No Drawings

ANTIBACTERIAL DEODORANT

This application claims priority to JP 2008-234776, filed Sep. 12, 2008.

BACKGROUND OF THE INVENTION

1. Field of the Invention

The present invention relates to an antibacterial deodorant that develops an antibacterial action as much as or more than high-level disinfectants (e.g., formalin, glutaraldehyde, and peracetic acid formulation) while posing the risk to an ecosystem as low as low-level disinfectants (e.g., quaternary ammonium salts, amphoteric surfactant, chlorhexidine) and that further has a deodorizing action.

2. Description of the Related Art

Various antibacterial agents have heretofore been proposed. Antibacterial agents having a strong antibacterial action, however, are limited in the purpose of use, the object for use, the range of use, and so on, and users are required to have a professional knowledge because antibacterial agents having a stronger antibacterial action generally tend to naturally show a higher toxicity to men and beasts. Therefore, not all persons have been able to use with ease antibacterial agents having a strong antibacterial action.

On the other hand, many deodorants also have been proposed, for example, deodorants utilizing various methods, e.g., chemically decomposing odor components (or malodorous substances) with chemicals, microorganisms, photocatalysts, or the like, physically adsorbing odor components with activated carbon, zeolite, silica gel, or the like, or masking odor components with perfumes.

By the way, in order to apply an antibacterial treatment to bedclothes or clothes at hospitals, nursing homes, and so on, much attention should be paid to safety, and deodorization is required as well as antibacterial action. However, even in such situations, there are no antibacterial deodorants that anyone can use with ease and that have both an antibacterial action and a deodorizing action at high levels.

Under such circumstances, the inventors of the present invention invented an antibacterial deodorant containing a cationic surfactant, a zwitterionic surfactant, a nonionic surfactant, and a hot water extract of beans, which is a liquid (ca. pH 4.5) that can be obtained by immersing beans in water, crushing them into a muddy state, heating the resultant at about 100° C. for 10 to 20 minutes and subsequently at about 80° C. for 20 to 60 minutes, filtering the resulting solution, adding water and a flocculating agent to the filtrate, heating the resulting mixture at about 100° C. for 20 to 60 minutes, and separating the resulting solids (see Japanese Patent No. 3529059 (Claims), below).

This antibacterial deodorant containing a bean hot water extract gained public favor because it has both a strong antibacterial action and a strong deodorizing action and is very user-friendly due to its very high safety to men and beasts. As a result, the inventors attained their desired end.

However, *Bacillus cereus*, *Bacillus anthracis* and small bacteria which form spores, and viruses have high resistance to drugs. In addition, sterilization by drugs cannot avoid the possibility of the appearance of resistant bacteria through screening. Moreover, as to deodorization, there are various substances which cause a bad smell (i.e., odorous components).

Therefore, there was a demand for the development of an antibacterial deodorant that has a stronger antibacterial action while maintaining a high safety with a low toxicity to men and beasts and that can be utilized for a wider variety of odorous components.

SUMMARY OF THE INVENTION

The present invention selects one or more deodorizing agents from among glycine, cysteine and glycylglycine, and incorporates the selected deodorizing agent(s) and a surfactant, thereby controlling the toxicity of the surfactant to men and beasts without inhibiting the antibacterial actions that the surfactant has inherently.

Glycine, cysteine, and glycylglycine each have a strong deodorizing action. The invention causes antibacterial deodorants to further have a deodorizing action by using such deodorizing agents.

Moreover, the invention increases the permeating ability, thereby enhancing both the antibacterial action and the deodorizing action by subjecting water to a treatment for fragmenting a cluster of the water and then adding a resulting active water as a diluent, or by preparing the diluent by incorporating alcohol to the active water.

In short, since the present invention prepared an antibacterial deodorant by incorporating a deodorizing agent and a surfactant, it can cause the antibacterial deodorant to reach very small spaces in the fibers of an object for antibacterial deodorization, for example, sheets of bedclothes and clothes, very fine irregularities on the surface of a bacteria itself and spaces in the bacteria because the surfactant naturally has high permeating ability.

Moreover, since the invention selected one or more members from among glycine, cysteine, and glycylglycine as a deodorizing agent, it can demonstrate an antibacterial action of a surfactant strongly by the action of such deodorizing agents while controlling the toxicity of the surfactant. Moreover, glycine, cysteine, and glycylglycine are harmless to men and beasts and are excellent in deodorizing action. Therefore, it is possible to impart also a deodorizing action to the antibacterial deodorants.

Hence, it can be applied to highly resistant bacteria and viruses and can be used for any objects with ease because of its high safety and, therefore, it is very convenient. In addition, it can serve for antibacterial treatment and deodorizing treatment simultaneously.

Glycine, cysteine, and glycylglycine, which are incorporated as deodorizing agents, exert a deodorizing action to different odorous components, respectively. Therefore, the application area of deodorization can be expanded by selecting and mixing two or more members among the above-mentioned deodorizing agents.

Because of adding, as a diluent, active water obtained by subjecting water to a treatment for fragmenting a cluster of the water, an antibacterial deodorizing action is improved through enhancement of the permeating ability of an antibacterial deodorant.

Since the diluent is prepared by adding, to active water, alcohol that has an action to reduce the surface tension of active water, the cluster of the diluent is fragmented by alcohol. Thus, the permeating ability of the antibacterial deodorant is further increased and, as a result, the antibacterial deodorizing action is improved drastically. As such, it results in significant advantages in practical use.

DETAILED DESCRIPTION OF THE INVENTION

The antibacterial deodorant of the present invention will be described in detail below.

The antibacterial deodorant of the present invention is an agent prepared basically by selecting one or more members from among glycine, cysteine, and glycylglycine as a deodorizing agent and incorporating such a deodorizing agent together with a surfactant.

As to the contents of the respective ingredients, if the content of the surfactant is less than 10 mg/l, even an antibacterial effect to general bacteria, which are among those of lowest drug resistance, cannot be observed, whereas if the content is more than 280000 mg/l, the toxicity to men and beasts cannot be controlled even in the case of using the maximum value of the deodorizing agent content provided below. Therefore, the content of the surfactant is preferably within the range of 10 to 280000 mg/g.

On the other hand, if the content of the deodorizing agent is less than 400 mg/l, the toxicity to men and beasts cannot be controlled even in the case of using the minimum value of the aforementioned surfactant content, whereas if the content is more than 150000 mg/l, the deodorizing agent crystallizes to precipitate and cause clouding. Therefore, the content of the deodorizing agent is preferably within the range of 400 to 150000 mg/l.

Examples of the surfactant include:
1) cationic surfactants, such as
Benzalkonium chloride
CAS No. 8001-54-5;
2) zwitterionic surfactant, such as
N-Lauryl β-Aminopropionic acid
Japan Cosmetic Industry Association Labeling Name: Lauraminopropionic acid; and
3) nonionic surfactants, such as
Propylene glycol
CAS No. 57-55-6.

These all have an excellent antibacterial action.

Glycine and cysteine, which are used for the present invention, are amino acids that serve as constituents of protein, and glycylglycine is a dipeptide made up of two glycine molecules linked by a peptide linkage. They are originally derived from organisms (vegetable and animal), but their origin is not the question in the present invention.

That is, they may be glycine, cysteine and glycylglycine which are produced by any of the extraction method in which a protein contained in an organism is decomposed and extracted, the chemical synthesis method in which a product is chemically synthesized, and the fermentation method in which a product is produced by fermentation using a microorganism.

Glycine, cysteine, and glycylglycine control the toxicity of a surfactant without inhibiting the antibacterial action of the surfactant and have a strong deodorizing action.

Although glycine, cysteine, and glycylglycine are naturally oxidized and gradually become unable to demonstrate their properties (an action of controlling the toxicity of a surfactant and a deodorizing action), the deterioration of the properties is prevented by the addition of an antioxidant.

As the antioxidant, ethylenediaminetetraacetic acid disodium salt dihydrate [CAS No.6381-92-6] (EDTA2Na), which is also a food additive, is preferable from the safety point of view.

By the addition of EDTA2Na, a metal ion as an inevitable impurity contained in a trace amount in an antibacterial deodorant is captured through complex formation, so that the antibacterial deodorant is stabilized and, as a result, it becomes possible to preserve the antibacterial deodorant for a long period of time.

Moreover, highly permeable active water may be added as a diluent to the above constitution (a deodorizing agent and a surfactant). The active water is a product obtained by subjecting water to a treatment for fragmenting a cluster of the water.

In normal water, a plurality of water molecules are associated and assembled together through hydrogen bonding to form a cluster (an aggregate of water molecules). Since the more the number of water molecules assembled and the greater the size of a cluster, the harder the entrance of the cluster into minute spaces of an object and naturally the lower the permeating ability. In contrast, water in which clusters are disassembled and fragmented has higher permeating ability.

Examples of the method for disassembling and fragmenting clusters include a method utilizing electricity, a method utilizing superfine air bubbles, and a method utilizing magnetism.

The method utilizing electricity is a method in which an electrolyte, such as salt, in a trace amount is added to water to obtain an aqueous solution and then a current is applied to an electrode soaked in the aqueous solution and active water (so called alkali ion water) generated around the electrode is taken out before electrolysis proceeds completely.

The method utilizing superfine air bubbles is a method in which superfine air bubbles (i.e., microbubbles or nanobubbles) are generated in water and clusters are disassembled by the bubbles, thereby being activated.

The method utilizing magnetism is a method in which a permanent magnet or an electromagnet is provided by a water flow channel and a magnetic force line perpendicular to the direction of the water flow is applied to water molecules, thereby activating water.

Furthermore, a diluent may also be prepared by incorporating, to the aforementioned active water, an alcohol that has an action of decreasing the surface tension of the active water.

The alcohol to be incorporated, the type of which is not concerned, may be aliphatic alcohols, alcohols of alicyclic compounds, alcohols of aromatic compounds, monohydric alcohols, polyhydric alcohols, and so on. Since the polarity of the hydroxyl group(s) of an alcohol molecule is involved in the decrease of the surface tension of active water caused by the alcohol, low molecular weight alcohols with the nonpolar portions of which are small in the construction of the alcohols are preferable in order to utilize the polarity. Ethyl alcohol, propyl alcohol and the like are preferable in the quality, the stability in obtainability, and the safety to men and beasts of alcohol.

That is, the diluent may basically be mere purified water, and when a stronger antibacterial action is wanted, active water may be used as the diluent, or the diluent may be prepared by mixing active water and alcohol, or the diluent may be prepared by mixing purified water, active water, and alcohol.

When mixing, the surface tension of the diluent decreases with an increase of the amount of active water in the diluent. While purified water and active water can be mixed freely, even if the amount of alcohol contained in a diluent of an amount of 1 exceeds 0.20, no decrease of the surface tension is observed any more and rather the safety in handling is impaired. The mixing weight ratio of purified water, active water, and alcohol is therefore preferably within the range of diluent [1.00]=purified water [1.00 to 0.00]+active water [0.00 to 1.00]+alcohol [0.00 to 0.20].

A further detailed description is made below with reference to Examples.

First, glutamine, glycine, tryptophan, methionine, lysine, cysteine, proline, arginine, valine, and glycylglycine were adopted for selection of proper deodorizing agents excellent in deodorizing action, and the following deodorization test 1 was performed for these.

<Deodorization Test 1>

First, an Erlenmeyer flask was hermetically sealed with a stopper, and while the sealed state was maintained, a microsyringe was inserted in the stopper. Then, a prescribed amount of an odorous component which had been confirmed by a preliminary test was injected into the flask with the microcyringe and then the odorous component was evaporated completely, so that the concentration of the odorous component in the air enclosed in the flask was adjusted to a prescribed initial concentration.

Next, while the hermetically sealed state was maintained, a prescribed amount of a deodorizing agent was injected into the flask prepared above with the microsyringe, and 30 minutes later the residual concentration of the odorous component within the flask was measured with a gas-detecting tube manufactured by Gastecs, Co., Ltd.

Ammonia, trimethylamine, methyl mercaptan, formaldehyde, acetaldehyde, isovaleric acid, acetic acid, toluene, and styrene were adopted as an odorous component. The initial concentration of each odorous component within the flask was determined with reference to a guideline of the Offensive Odor Control Law announced by the Environment Agency.

As to each of the deodorizing agents, an aqueous solution prepared by adjusting the concentration of the agent to 10% by weight with purified water was used and the amount of the aqueous solution injected into the flask was determined to be 0.2 ml.

The results are set forth in the following Tables 1 to 10.

TABLE 1

| | Glutamine | | |
|---|---|---|---|
| | Initial concentration (ppm) | Concentration after 30 minutes (ppm) | Reduction (%) |
| Ammonia | 100 | 90 | 10 |
| Trimethylamine | 20 | 18 | 10 |
| Methyl mercaptan | 10 | 8 | 20 |
| Formaldehyde | 10 | 9 | 10 |
| Acetaldehyde | 10 | 10 | 0 |
| Isovaleric acid | 10 | 9 | 10 |
| Acetic acid | 20 | 18 | 10 |
| Toluene | 100 | 100 | 0 |
| Styrene | 100 | 100 | 0 |

TABLE 2

| | Glycine | | |
|---|---|---|---|
| | Initial concentration (ppm) | Concentration after 30 minutes (ppm) | Reduction (%) |
| Ammonia | 100 | 0 | 100 |
| Trimethylamine | 20 | 0 | 100 |
| Methyl mercaptan | 10 | 0 | 100 |
| Formaldehyde | 10 | 3 | 70 |
| Acetaldehyde | 10 | 2 | 80 |
| Isovaleric acid | 10 | 1 | 90 |
| Acetic acid | 20 | 2 | 90 |
| Toluene | 100 | 40 | 60 |
| Styrene | 100 | 40 | 60 |

TABLE 3

| | Tryptophan | | |
|---|---|---|---|
| | Initial concentration (ppm) | Concentration after 30 minutes (ppm) | Reduction (%) |
| Ammonia | 100 | 50 | 50 |
| Trimethylamine | 20 | 10 | 50 |
| Methyl mercaptan | 10 | 10 | 0 |
| Formaldehyde | 10 | 9 | 10 |
| Acetaldehyde | 10 | 9 | 10 |
| Isovaleric acid | 10 | 10 | 0 |
| Acetic acid | 20 | 18 | 10 |
| Toluene | 100 | 100 | 0 |
| Styrene | 100 | 100 | 0 |

TABLE 4

| | Methionine | | |
|---|---|---|---|
| | Initial concentration (ppm) | Concentration after 30 minutes (ppm) | Reduction (%) |
| Ammonia | 100 | 70 | 30 |
| Trimethylamine | 20 | 18 | 10 |
| Methyl mercaptan | 10 | 10 | 0 |
| Formaldehyde | 10 | 9 | 10 |
| Acetaldehyde | 10 | 9 | 10 |
| Isovaleric acid | 10 | 10 | 0 |
| Acetic acid | 20 | 18 | 10 |
| Toluene | 100 | 90 | 10 |
| Styrene | 100 | 90 | 10 |

TABLE 5

| | Lysine | | |
|---|---|---|---|
| | Initial concentration (ppm) | Concentration after 30 minutes (ppm) | Reduction (%) |
| Ammonia | 100 | 90 | 10 |
| Trimethylamine | 20 | 18 | 10 |
| Methyl mercaptan | 10 | 10 | 0 |
| Formaldehyde | 10 | 10 | 0 |
| Acetaldehyde | 10 | 9 | 10 |
| Isovaleric acid | 10 | 10 | 0 |
| Acetic acid | 20 | 20 | 0 |
| Toluene | 100 | 100 | 0 |
| Styrene | 100 | 100 | 0 |

TABLE 6

| | Cysteine | | |
|---|---|---|---|
| | Initial concentration (ppm) | Concentration after 30 minutes (ppm) | Reduction (%) |
| Ammonia | 100 | 0 | 100 |
| Trimethylamine | 20 | 0 | 100 |
| Methyl mercaptan | 10 | 10 | 0 |
| Formaldehyde | 10 | 8 | 20 |
| Acetaldehyde | 10 | 10 | 0 |
| Isovaleric acid | 10 | 8 | 20 |
| Acetic acid | 20 | 16 | 20 |
| Toluene | 100 | 90 | 10 |
| Styrene | 100 | 90 | 10 |

TABLE 7

| Proline | | |
|---|---|---|
| Initial concentration (ppm) | Concentration after 30 minutes (ppm) | Reduction (%) |
| Ammonia | 100 | 90 | 10 |
| Trimethylamine | 20 | 19 | 5 |
| Methyl mercaptan | 10 | 10 | 0 |
| Formaldehyde | 10 | 10 | 0 |
| Acetaldehyde | 10 | 8 | 20 |
| Isovaleric acid | 10 | 10 | 0 |
| Acetic acid | 20 | 20 | 0 |
| Toluene | 100 | 100 | 0 |
| Styrene | 100 | 100 | 0 |

TABLE 8

| Arginine | | |
|---|---|---|
| Initial concentration (ppm) | Concentration after 30 minutes (ppm) | Reduction (%) |
| Ammonia | 100 | 90 | 10 |
| Trimethylamine | 20 | 19 | 5 |
| Methyl mercaptan | 10 | 10 | 0 |
| Formaldehyde | 10 | 10 | 0 |
| Acetaldehyde | 10 | 9 | 10 |
| Isovaleric acid | 10 | 10 | 0 |
| Acetic acid | 20 | 17 | 15 |
| Toluene | 100 | 100 | 0 |
| Styrene | 100 | 100 | 0 |

TABLE 9

| Valine | | |
|---|---|---|
| Initial concentration (ppm) | Concentration after 30 minutes (ppm) | Reduction (%) |
| Ammonia | 100 | 90 | 10 |
| Trimethylamine | 20 | 19 | 5 |
| Methyl mercaptan | 10 | 10 | 0 |
| Formaldehyde | 10 | 10 | 0 |
| Acetaldehyde | 10 | 10 | 0 |
| Isovaleric acid | 10 | 10 | 0 |
| Acetic acid | 20 | 20 | 0 |
| Toluene | 100 | 100 | 0 |
| Styrene | 100 | 100 | 0 |

TABLE 10

| Glycylglycine | | |
|---|---|---|
| Initial concentration (ppm) | Concentration after 30 minutes (ppm) | Reduction (%) |
| Ammonia | 100 | 90 | 10 |
| Trimethylamine | 20 | 18 | 10 |
| Methyl mercaptan | 10 | 8 | 20 |
| Formaldehyde | 10 | 9 | 10 |
| Acetaldehyde | 10 | 10 | 0 |
| Isovaleric acid | 10 | 9 | 10 |
| Acetic acid | 20 | 18 | 10 |
| Toluene | 100 | 100 | 0 |
| Styrene | 100 | 100 | 0 |

As described above, the deodorization test 1 revealed that three compounds, glycine, cysteine, and glycylglycine, were useful as deodorizing agents.

As shown in Table 2, glycine exhibited an excellent deodorizing action particularly to ammonia, trimethylamine, and methyl mercaptan among the selected odorous components, and good results were obtained also for acetaldehyde, isovaleric acid, and acetic acid.

Cysteine exhibited an excellent deodorizing action to ammonia and trimethylamine as shown in Table 6.

As shown in Table 10, glycylglycine exhibited a good deodorizing action to ammonia, trimethylamine, and methyl mercaptan, and also exhibited an excellent deodorizing action to formaldehyde, acetaldehyde, isovaleric acid, acetic acid, toluene, and styrene.

Next, antibacterial deodorant 1 mentioned in the preceding background art section and having the composition shown below, and antibacterial deodorant 2 having the following composition containing the above-mentioned three deodorizing agents were prepared by using purified water as a diluent.

<Antibacterial Deodorant 1>

| * Surfactant | |
|---|---|
| Benzalkonium chloride | 2000 mg/l |
| N-Lauryl β-Aminopropionic acid | 500 mg/l |
| Propylene glycol | 2000 mg/l |
| * Bean hot water extract | 2200 mg/l. |
| * Antioxidant | |
| Ethylenediaminetetraacetic acid disodium salt dehydrate | 1000 mg/l |

<Antibacterial Deodorant 2>

| * Surfactant | |
|---|---|
| Benzalkonium chloride | 2000 mg/l |
| N-Lauryl β-Aminopropionic acid | 500 mg/l |
| Propylene glycol | 2000 mg/l |
| * Deodorizing agent | |
| Glycine | 2000 mg/l |
| Cysteine | 200 mg/l |
| Glycylglycine | 40 mg/l |
| * Antioxidant | |
| Ethylenediaminetetraacetic acid disodium salt dehydrate | 1000 mg/l |

<Deodorization Test 2>

Deodorization test 2 was performed under the same conditions as those of deodorization test 1 except for replacing the aqueous solution of the deodorizing agent used in deodorizing test 1 by antibacterial deodorant 1 or 2.

The results are shown in Tables 11 and 12.

TABLE 11

| Antibacterial deodorant 1 | | |
|---|---|---|
| Initial concentration (ppm) | Concentration after 30 minutes (ppm) | Reduction (%) |
| Ammonia | 100 | 5 | 90 |
| Trimethylamine | 20 | 3 | 75 |
| Methyl mercaptan | 10 | 5 | 20 |
| Formaldehyde | 10 | 3 | 40 |
| Acetaldehyde | 10 | 3 | 50 |
| Isovaleric acid | 10 | 4 | 50 |

TABLE 11-continued

| | Antibacterial deodorant 1 | | |
|---|---|---|---|
| | Initial concentration (ppm) | Concentration after 30 minutes (ppm) | Reduction (%) |
| Acetic acid | 20 | 3 | 75 |
| Toluene | 100 | 50 | 40 |
| Styrene | 100 | 50 | 40 |

TABLE 12

| | Antibacterial deodorant 2 | | |
|---|---|---|---|
| | Initial concentration (ppm) | Concentration after 30 minutes (ppm) | Reduction (%) |
| Ammonia | 100 | 0 | 100 |
| Trimethylamine | 20 | 0 | 100 |
| Methyl mercaptan | 10 | 0 | 100 |
| Formaldehyde | 10 | 0 | 100 |
| Acetaldehyde | 10 | 0 | 100 |
| Isovaleric acid | 10 | 0 | 100 |
| Acetic acid | 20 | 0 | 100 |
| Toluene | 100 | 0 | 100 |
| Styrene | 100 | 0 | 100 |

As described above, according to the deodorization test 2, the antibacterial deodorant 2, in which three deodorizing agents, i.e., glycine, cysteine and glycylglycine, were incorporated, exhibited an excellent deodorization effect for methyl mercaptan, formaldehyde, acetaldehyde, isovaleric acid, toluene, and styrene, for which a sufficient deodorization effect was not obtained by the antibacterial deodorant 1, and moreover, the antibacterial deodorant 2 exhibited an excellent deodorization effect for all the odorous components used in this test. Thus, it was confirmed that the antibacterial deodorant 2 exerts a deodorizing action for a wide variety of odorous components.

For the antibacterial deodorants 1 and 2, the following antibacterial test, virus inactivation tests 1 and 2, and fungus resistance test were carried out.

Moreover, a diluent was prepared by mixing purified water, active water and ethanol in a weight ratio of 0.90:0.07:0.03, and by the use of the diluent the following antibacterial test, virus inactivation tests 1 and 2, and fungus resistance test were carried out for an antibacterial deodorant 3 prepared by incorporating a surfactant and deodorizing agents, like the antibacterial deodorant 2.

<Antibacterial Test>

Working solutions were prepared by mixing suspensions of each of the bacteria, provided in the following table and prepared at a prescribed bacteria amount, and each of the aforementioned antibacterial deodorants in a predetermined ratio. After being left at rest for a prescribed time at room temperature, the working solutions were each inoculated in a prescribed amount on a standard agar medium, followed by cultivation at 35° C. for 48 hours. Then, the number of colonies formed was counted and it was defined as the amount of living bacteria.

Moreover, the same test was repeated by replacing the antibacterial deodorant by a sterilized phosphate buffered saline, and the resulting amount of living bacteria was used as a control.

The amounts of living bacteria resulting from the use of each antibacterial deodorant and the results of comparison to the control are shown in the following Table 13.

TABLE 13

| | The amount of | Result | | |
|---|---|---|---|---|
| Name of bacteria | living bacteria of control (cfu/ml) | Antibacterial deodorant 1 | Antibacterial deodorant 2 | Antibacterial deodorant 3 |
| Methicillin resistant staphylococcus aureus | $1.1 \times 10^6$ | ◉ | ◉ | ◉ |
| Escherichia coli | $2.6 \times 10^6$ | ◉ | ◉ | ◉ |
| Pseudomonas aeruginosa | $1.0 \times 10^8$ | ◉ | ◉ | ◉ |
| Trichophyton | $2.8 \times 10^2$ | ◉ | ◉ | ◉ |
| Legionella | $8.3 \times 10^5$ | ◉ | ◉ | ◉ |
| Salmonella | $1.0 \times 10^6$ | ◉ | ◉ | ◉ |
| Candida | $2.0 \times 10^6$ | ◉ | ◉ | ◉ |
| Bacillus subtilis spore | $4.2 \times 10^5$ | ○ | ○ | ◉ |
| Bacillus cereus spore | $1.0 \times 10^4$ | X | X | ◉ |

◉: Almost all bacteria in a working solution dead and no colony was formed.
○: The number of colonies (the amount of living bacteria) decreased to about 1/100 of the control.
X: The amount of living bacteria did not change.

As described above, according to this antibacterial test, both the conventional antibacterial deodorant 1 and the antibacterial deodorant 2 according to the present invention exhibited significantly excellent antibacterial actions to methicillin resistant *staphylococcus aureus, escherichia coli, pseudomonas aeruginosa, trichophyton, legionella, salmonella*, and *candida*. Moreover, also as to *bacillus subtilis* spore, which is highly resistant, the comparison with the control revealed that the antibacterial deodorants were able to kill bacteria in the working solutions to about 1/100. Thus, it was confirmed that the antibacterial agents were effective in practical use.

Moreover, bacillus cereus spore had extremely high resistance, so that both the antibacterial deodorants 1 and 2 failed to exhibit effect. It was confirmed, however, that the antibacterial deodorant 3, in which active water and ethanol had been incorporated, exhibited a significantly excellent antibacterial action also to bacillus cereus spore.

<Virus Inactivation Test 2>

Working solutions were prepared by mixing suspensions of avian flu virus and each of the aforementioned antibacterial deodorants in a predetermined ratio. After being left at rest for a prescribed time at room temperature, the working solutions were diluted with sterilized phosphate buffered saline stepwise to 10 times. At every dilution, each solution was inoculated in a prescribed amount on three 10-day-old embryonated eggs.

The embryonated eggs after the inoculation were cultured at 37° C. for 48 hours, and then the occurrence of virus proliferation in the chorioallantoic liquid was checked by a 0.5□ hen hemagglutination (HA) test.

The viral infectivity was calculated by the Reed and Muench method.

Moreover, a similar test was conducted by using sterilized phosphate buffered saline instead of the antibacterial deodorant, and the obtained viral infectivity was used as a control.
<Virus Inactivation Test 2>

Working solutions were prepared by mixing a suspension of feline calicivirus and each of the aforementioned antibacterial deodorants in a predetermined ratio. After being left at rest for a predetermined time at room temperature, the working solutions were diluted to 1000 times with a cell maintenance medium.

Cells used were subjected to monolayer culture in a microplate (96 holes) for tissue culture by the use of a cell proliferation medium, and then the cell proliferation medium was removed and 0.1 ml of cell maintenance media was added into every hole.

Then, 0.1 ml of the diluted liquid of the aforementioned working solution was inoculated into every four holes, followed by cultivation in a 37° C. carbon dioxide gas incubator for 4 to 7 days. Thereafter, the occurrence of the alteration of cellular morphology was checked by using an inverted phase contrast microscope. Moreover, a 50% tissue culture infective dose was calculated by the Reed and Muench method and it was converted into a viral infectivity per milliliter of working solution.

Moreover, a similar test was conducted by using purified water instead of the antibacterial deodorant, and the obtained viral infectivity was used as a control.

The results of the virus inactivation tests 1 and 2 are shown in the following Table 14.

TABLE 14

| | | Result | | |
|---|---|---|---|---|
| Virus name | Viral infectivity of control | Antibacterial deodorant 1 | Antibacterial deodorant 2 | Antibacterial deodorant 3 |
| Avian flu virus | $1.0 \times 10^8$ ($EID_{50}/0.1$ ml) | Δ | Δ | ◎ |
| Feline calicivirus | $1.0 \times 10^7$ ($EID_{50}$/ml) | X | X | ○ |

◎: The viral infectivity decreased to 1/106 the control.
○: The viral infectivity decreased to 1/104 the control.
Δ: The viral infectivity decreased to 1/10 the control.
X: There was no change in viral infectivity.

As shown above, according to the virus inactivation tests 1 and 2, while the antibacterial deodorants 1 and 2 demonstrate a slight deactivating action against avian flu virus, they have no inactivation effects against feline calicivirus.

It, however, was confirmed that the antibacterial deodorant 3 demonstrated a great inactivating action to both the viruses.
<Fungus Resistance Test>

With reference to the testing method for fungus-proof coating materials provided in JIS Z2911 (2000) and with some modifications in test conditions, a fungus resistance test was performed for the antibacterial deodorants 1, 2 and 3.

Namely, five fungi, *Aspergillus Niger* FERM S-2, *Penicillium Funiculosum* FERM S-6, *Cladosporium Cladosporioides* FERM S-8, *Aureobasidium Pullulans* FERM S-9, and *Gliocladium Virens* FERM S-10, were selected as fungi for test, and a mixed spore suspension of the five fungi was prepared.

On the other hand, a regular plane culture medium was used as a culture medium for test. A test piece was prepared by cutting a filter paper into a circle with a diameter of 30 mm, uniformly spraying 3 ml of the antibacterial deodorant diluted to 30 times with purified water to the circular filter paper, and drying it.

Then the dried test piece was attached to the center of the culture surface of the plane culture medium, and 1 ml of the mixed spore suspension was sprayed uniformly onto the surface of the culture medium and the test piece. The resultant was covered and was cultivated at a temperature of about 28° C. for 28 days.

Moreover, a similar test was conducted by replacing the antibacterial deodorant by purified water, and the obtained result was used as a control.

The result was evaluated in accordance with a prescribed method.

The evaluations of the results of the cases using the respective antibacterial deodorants are shown in the following Table 15.

TABLE 15

| | Result | | |
|---|---|---|---|
| Control | Antibacterial deodorant 1 | Antibacterial deodorant 2 | Antibacterial deodorant 3 |
| 2 | 0 | 0 | 0 |

Indication of the test result in accordance with JIS Z2911
0: No growth of a hypha is observed in the inoculated part of a test piece.
1: The area of the hypha growing portion observed in the inoculated part of a test piece is not greater than ⅓ of the whole area.
2: The area of the hypha growing portion observed in the inoculated part of a test piece is greater than ⅓ of the whole area.

As shown above, according to the fungus resistance test, the antibacterial deodorants 1, 2, and 3 exhibited excellent fungus resistance.

Moreover, from the results of the fungus resistance test and common technical knowledge, all the antibacterial deodorants are observed to be excellent in durability of their properties, and it is apparent that this durability will be demonstrated similarly also with respect to an antibacterial action.

What is claimed is:
1. An antibacterial deodorant prepared by mixing a surfactant and glycine and glycylglycine.
2. An antibacterial deodorant prepared by mixing a surfactant and glycine, cysteine and glycylglycine.

3. The antibacterial deodorant according to claim 1, to which active water obtained by subjecting water to a treatment for fragmenting a cluster of the water has been added as a diluent.

4. The antibacterial deodorant according to claim 3, wherein the diluent is prepared by adding, to active water, alcohol that has an action of reducing the surface tension of the active water.

5. The antibacterial deodorant according to claim 1, wherein the surfactant is selected from the group consisting of a cationic surfactant, a zwitterionic surfactant and a nonionic surfactant.

6. The antibacterial deodorant according to claim 5, wherein the cationic surfactant is benzalkonium chloride, the zwitterionic surfactant is N-lauryl β-aminopropionic acid and the nonionic surfactant is propylene glycol.

* * * * *